United States Patent [19]

Assarsson et al.

[11] 3,993,551

[45] Nov. 23, 1976

[54] PROCESS FOR COCROSSLINKING WATER SOLUBLE POLYMERS AND PRODUCTS THEREOF

[75] Inventors: Per G. Assarsson, Montclair, N.J.; Paul A. King, Warwick, N.Y.

[73] Assignee: Union Carbide Corporation, New York, N.Y.

[22] Filed: June 30, 1975

[21] Appl. No.: 592,130

Related U.S. Application Data

[63] Continuation-in-part of Ser. No. 395,553, Sept. 10, 1973, Pat. No. 3,893,143, which is a continuation of Ser. No. 152,370, June 11, 1971, abandoned.

[52] U.S. Cl. .......................... 204/159.14; 128/284; 128/285; 204/159.12; 260/2 EN; 260/9; 260/13; 260/874; 260/895; 260/897 R; 260/901
[51] Int. Cl.² ...................... C08F 8/00; C08D 1/00
[58] Field of Search .................. 204/159.12, 159.14; 260/29.6 NR, 874

[56] References Cited

UNITED STATES PATENTS

| | | | |
|---|---|---|---|
| 3,264,202 | 8/1966 | King | 204/159.14 |
| 3,470,078 | 9/1969 | King | 204/159.14 |
| 3,664,343 | 5/1972 | Assarsson | 204/159.14 |
| 3,898,143 | 5/1975 | Assarsson et al. | 204/159.12 |

*Primary Examiner*—Richard B. Turer
*Attorney, Agent, or Firm*—William Raymond Moran

[57] ABSTRACT

Poly(ethylene oxide) and at least one other water soluble polymer are conveniently cocrosslinked by exposing aqueous systems of the polymers to high energy irradiation. The resulting products are insoluble hydrophilic gels which can contain or when dried absorb large quantities of aqueous fluids and hence are useful as absorbing media for disposable absorbent articles, agricultural applications and the like.

8 Claims, No Drawings

PROCESS FOR COCROSSLINKING WATER SOLUBLE POLYMERS AND PRODUCTS THEREOF

This application is a continuation-in-part of U.S. Pat. application Ser. No. 395,553, now U.S. Pat. No. 3,893,143 entitled "Process For Cocrosslinking Water Soluble Polymers and Products Thereof" filed Sept. 10, 1973 by P. G. Assarsson et al. Application Ser. No. 395,553 is in turn a continuation of application Ser. No. 152,370 filed June 11, 1971, now abandoned.

This invention relates in general to a process for cocrosslinking water soluble polymers and the products obtained thereby. In one aspect, this invention relates to a process for cocrosslinking poly(ethylene oxide) and at least one other water soluble polymer. In a further aspect, this invention relates to cocrosslinked polymers of poly(ethylene oxide) and other water soluble polymers.

It has been reported in the literature that water solutions of poly(ethylene oxide) can be crosslinked by exposure to ionizing radiation. For example, in U.S. Pat. No. 3,264,202 ethylene oxide polymers were crosslinked by exposure of a solution of the polymer to irradiation to provide a gel-like material which was essentially water insoluble. The gel-like material then can be dried to remove essentially all the water. Due to its ability to absorb large quantities of fluids, crosslink poly(ethyelene oxide) is useful for a wide variety of applications. For instance, it is useful as a plant growth medium as disclosed in U.S. Pat. No. 3,336,129, as a burn and wound dressing as set forth in U.S. Pat. No. 3,419,006 and as a cooling medium as disclosed in U.S. Pat. No. 3,545,230. Prior to the present invention, however, cocrosslinking of poly(ethylene oxide) with other water soluble polymers which do not have the ethylene ether unit has not been reported.

It has now been found that aqueous systems of poly(ethylene oxide) and other water soluble polymers can be cocrosslinked to provide insoluble hydrophilic gels. In particular, it has been found that heterogeneous systems wherein two or more aqueous phases exits can be cocrosslinked to provide a gel which has a homogeneous appearance and properties which are different from gels prepared by crosslinking solutions of the individual polymers.

It is therefore an object of this invention to provide a process for cocrosslinking water soluble polymers. Another object of this invention is to provide a process for cocrosslinking poly(ethylene oxide) and other water soluble polymers. A further object of this invention is to provide a process for cocrosslinking heterogeneous aqueous systems of water soluble polymers. Another object of this invention is to provide a process for cocrosslinking homogeneous aqueous solutions of poly(ethylene oxide) and water soluble polymers. A still further object is to provide insoluble hydrophilic gels of cocrosslinked water soluble polymers. These and other objects will be readily become apparent to those skilled in the art in the light of the teachings herein set forth.

In its broad aspect, this invention is directed to a process for cocrosslinking water soluble polymers and to the products obtained therefrom. The process of this invention comprises cocrosslinking, such as by irradiation, two or more water soluble polymers selected from the group of non-ionic, cationic and anionic polymers. Illustrative polymers which can be cocrosslinked by the process of this invention include, among others poly(ethylene oxide) and those from the group (a), consisting of starch, methylcellulose, ethylcellulose, hydroxyethylcellulose, hydroxypropyl-methylcellulose, ethylhydroxyethylcellulose, ethyl-methylcellulose, hydroxyethyl-methylcellulose, carboxymethylcellulose and salts thereof, and carboxymethylhydroxyethylcellulose salts, polyvinyl alcohol, polyvinyl pyrrolidone, polyacrylamide, poly-4-vinyl-n-butylpyridinium bromide, polyvinylmethyl ether, vinylmethyl ether-maleic anhydride copolymer and gelatin or the group (b) consisting of polyacrylic acid, ammonium polyacrylate and ethylene maleic anhydride copolymer. The process comprises the steps of:

a. forming an aqueous solution of two or more of the water soluble polymers,
b. adjusting the pH of the solution to within the range of from about 2 to about 11 for polymers of group (a), and to within the range of greater than 4.0 and less than 9.0 for the polymers of group (b),
c. intimately mixing the solution to form a homogeneous, or heterogeneous micro-phase system, and
d. before any substantial phase separation, exposing the solution to ionizing radiation for a period of time to form a gellike material.

The cocrosslinked products of this invention, as hereinbefore indicated, are insoluble hydrophilic gels which have a homogeneous appearance and properties which are different from gels prepared by crosslinking solutions of the individual polymers. For instance, it has been observed that films prepared from the gels of this invention, for the most part, have intermediate or greater strength, stability and toughness, compared to films prepared by crosslinking the individual polymers.

In practice, the cocrosslinked, insoluble, hydrophilic gels of this invention are conveniently prepared by forming an aqueous system of poly(ethylene oxide) and at least one of the other water soluble polymers. The majority of the polymers do not form a homogeneous system and hence, the polymer must be cocrosslinked before any substantial phase separation occurs. In order to cocrosslink poly(ethylene oxide) and the polymers of group (a) above, it has been observed that the pH should be within the range of from about 2 to about 11. For cocrosslinking of poly(ethylene oxide) and the polymers of group (b) the pH should be greater than 4.0 and less than 9.0.

Mixing of the polymer solution to form a homogeneous of heterogeneous microphase system can be accomplished by a variety of methods. The mixing must be of such a degree to insure that no substantial phase separation occurs before the polymers are cocrosslinked. For example, ordinary laboratory stirrers have been found suitable to achieve the desired results.

Solutions containing various ratios of poly(ethylene oxide) to the other water, soluble polymers have been successfully cocrosslinked. For example, poly(ethylene oxide) can be present in as little as 1 per cent, based on the total weight of the combined polymers, or as high as 99 per cent.

In practice, the aqueous solutions, prior to cocrosslinking can contain up to about 50 per cent by weight of the combined polymers. Preferably, solutions containing from about 1 to about 20 per cent are employed.

The water-soluble poly(ethylene oxide) polymers which are cocrosslinked with the other polymers will usually have a molecular weight such that the reduced viscosity of the polymer will be within the range of from about 0.5 to about 75, and higher, and preferably from about 1 to about 60, or an aqueous viscosity of 25° C. of from about 225 centipoises measured at a 5 weight per cent concentration, to about 12,000 centipoises, and higher measured at a 1 weight per cent concentration.

The water-insoluble hydrophilic cocrosslinked polymers are produced by subjecting the above-described water soluble polymers, to sufficient ionizing radiation to crosslink and insolubilize the polymer forming thereby a water-insoluble hydrophilic products. As used herein, the term "ionizing radiation" includes that radiation which has sufficient energy to cause electronic excitation and/or ionization in the polymer molecules or in the solvent (where a solvent is employed) but which does not have sufficient energy to affect the nuclei of the constituent atoms. Convenient sources of suitable ionizing radiation are gamma ray-producing radioactive isotopes such as $Co^{60}$ and $Cs^{137}$, spent nuclear fuel elements, X-rays such as those produced by conventional X-ray machines, and electrons produced by such means as Van de Graaff accelerators, linear electron accelerators, resonance transformers, and the like. Suitable ionizing radiation for use in the present invention will generally have an energy level in the range from about 0.05 MeV to about 20 MeV.

The irradiation of the non-crosslinked (water soluble) polymers can be carried out in the solid phase or in solution. Solid polymers can be irradiated in the air, in a vaccum, or under various gaseous atmospheres, while irradiation in solution can be carried with the polymers dissolved in water, or in mixtures of water and water-miscible organic solvents. Any conventional method can be used to bring the solid polymer or polymer solution into contact with the ionizing radiation. Suitable methods are well known and understood by those skilled in the art.

The exact amount of ionizing radiation to which the polymers must be subjected depends on a number of variables. In general, when irradiation is carried out at relatively low rates and in the presence of free radical scavengers such as oxygen, extremely high total doses are required to produce the water-insoluble hydrophilic polymers. On the other hand, when the irradiation is carried out under conditions which favor the relatively long existence of the free radicals produced, for example, when the irradiation is carried out with a high dose rate, in the absence of oxygen, or in solution where oxygen is rapidly used up, the formation of water-insoluble hydrophilic polymers take place readily. The preferred method for producing the water-insoluble hydrophilic polymers is to carry out the irradiation in an aqueous solution of the water-soluble polymers while employing ionizing radiation having an energy level in the range of about 0.10 MeV. to about 20 MeV. at a total dose of between about 0.05 and 10 megarads. In addition to cocrosslinking by ionizing radiation, the polymers can also be cocrosslinked by chemical methods. For example, peroxides such as, acetyl peroxide, in the presence of a multifunctional reagent such as, divinylbenzene, have been successfully employed.

The terms "insoluble" or "insolubilize" as employed throughout the specification are utilized herein to refer to the formation of a product, a variable portion of which is essentially insoluble in water, depending upon the degree of crosslinking. By the term "cocrosslinking" is meant insolubilization of the polymeric mixture wherein like or dislike polymer chains are linked by covalent bonding at one or more cites along the chain.

Certain of the polymers may become entrapped in and among the crosslinked polymers without actually being linked themselves. This entrapment will also contribute to the insolubility of the polymers. These polymers can swell and adsorb many times their weight in water because they are also hydrophilic.

The insoluble, hydrophilic cocrosslinked polymers or gels which are prepared by the process of this invention are useful in a wide variety of fields. For example, the gels can contain, or when dried absorb, large quantities of aqueous fluids and hence are useful as absorbing media for disposable absorbent articles, agricultural applications, such as moisture retainers, and the like. They are of particular interest as an absorbing media for diapers, or catamenial devices such as sanitary napkins and tampons.

Although disposable absorbent articles for the absorption of body fluids have been in use for many years they have not always been completely satisfactory to the user. Numerous materials, variations in construction, and absorbents have all been reported in the literature. However, many products currently on the market suffer from the disadvantage of having poor or inferior absorption properties. In the past, the usual method employed to increase absorption characteristics was to add inexpensive materials which had modest or low absorptive capacity such as fluffed wood pulp and the like contained between layers of moisture permeable fabrics. While satisfactory as absorbents for fluids, in many instances, the article would be bulky and not comfortable. For example, diapers must have a minimum thickness to insure sufficient absorption of body fluids. If, however, the absorbing material has a low absorptive characteristic to be acceptable, the diaper would undoubtedly be bulky and not conform properly to the body contours.

Moreover, one of the major disadvantages of the products commercially available today, is that while they may have relatively high absorptive capacities, the absorbing media, if subjected to pressure, can release a portion of the absorbed liquid. This is due to the fact that the liquid is physically entrapped within a fibrous structure and a relatively slight pressure is all that is needed to cause the absorbent media and the liquid to separate. This, of course, is highly undesirable, particularly in catamenial devices.

The insoluble hydrophilic polymers prepared by the process of this present invention, are particularly useful because they possess the ability to incorporate very large amounts of water in the order of 25 to 1,000 times their dry weight. Moreover, in addition to possessing the ability to incorporate large amounts of water, they are insoluble in water irrespective of temperature and will retain liquids, solutions and suspensions. In general, the aforementioned gels are useful for increasing the absorbency of any known or commercially available disposable, article. For example, the hydrogels can be incorporated into diapers of the type disclosed in U.S. Pat. Nos. 2,788,003; 2,860,637; 3,306,293; and 2,667,168. Similarly, they can be incorporated into tampons or sanitary napkins of the type disclosed in U.S. Pat. Nos. 3,121,427; 3,070,095 and the like. The gels can be employed in a wide variety of ways, such as, for example, as a powder dispersed in and bonded to a cellulosic similar substrate, or as a film of the hydrogel sandwiched between layers of the supporting structure. Any of the several known methods can be employed to affix the film or powdered hydrogel to the substrate.

In general, the amount of hydrophilic polymer employed will be dependent upon the particular absorbent article and its intended use. In practice, it has been observed that disposable absorbent articles can be prepared containing from about 2 to about 98 weight per cent, of said hydrophilic polymers, based on the total weight of said article.

In some instances, it may be desirable to stabilize the cocrosslinked products prepared by the process of this invention. It has been observed that poly(ethylene imine) is an excellent stabilizer. These are polymers prepared from ethylene imine and which contain in a major amount the recurring unit:

and in a minor amount the recurring unit:

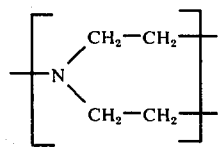

In practice poly(ethylene imine) polymers having molecular weights of from about 10,000 to about 100,000 are ideally suited for use in the instant invention. Particularly preferred are the poly(ethylene imine) polymers having molecular weight of from about 20,000 to about 80,000. These polymers are prepared by processes known in the literature and are commercially available.

In practice, the poly(ethylene imine) stabilizer is employed in a stabilizing amount. By the term "stabilizing amount" as employed throughout the specification and claims, is meant that quantity of poly(ethylene imine) which when admixed with the polymer will decrease the rate of degradation over that of the unstabilized polymer. It has been observed that as little as about 0.01 weight per cent based on the solid polymer, will effectively stabilize the polymer against degradation. of from about 0.2 to about 3.0 weight per cent is preferred. However, if desired, concentrations of poly(ethylene imine) as high as 50 weight per cent can be employed.

EXAMPLE I

A stock solution of poly(ethylene oxide) was prepared by using a commercial coagulant grade resin sold by Union Carbide Corporation under the trademark "POLYOX" and having a molecular weight in excess of $10^6$. This resin was dissolved by stirring in water to give a concentration of 4 per cent then shearing the resulting high viscosity solution in a high speed mixing device to a viscosity of 560,000 cps.

A stock solution of hydroxy ethyl cellulose was also prepared by using a commercial grade resin (Cellulosize QP 100-M from Union Carbide Corporation). Different weight ratios (poly(ethylene oxide) : hydroxyethyl cellulose) of 9:1, 3:1, 1:1 and 1:9 were prepared by simple addition of appropriate volumes under stirring until a homogeneous blend was obtained.

At least five portions of 10 cubic centimeters of each weight ratio mixture were poured into standard plastic petri dishes and each dish irradiated using a van de Graff electron accelerator having an energy of 1 MeV to different total doses of .2, .4, .6, .8 and 1.0 Mrad. Each irradiated mixture was allowed to dry in ambient room temperature and humidity conditions overnight. The resulting dry films were each analyzed for per cent insolubilized and saline water absorption capacity in the following manner:

a. per cent insoluble: about .2 grams of the dried polymer is accurately weighed out and placed in jars containing 200 cubic centimeters of a 10 per cent water in methanol mixture. The jar is then placed on a roller mill for constant agitation for approximately 16 to 20 hours after which time the swollen gel is placed in a drying oven. The dried solid is weighed and the per cent insolubilized gel calculated in accordance with the following equation:

$$\frac{\text{non-extractable weight}}{\text{original weight}} \times 100 = \text{per cent insoluble gel}$$

conversely, the extracted material or per cent soluble content is calculated as follows:

$$\frac{100 - \text{non-extractable weight}}{\text{original sample weight}} \times 100 = \text{per cent soluble content}$$

In cases where the cocrosslinked dried polymer was not soluble in this methanol-water extraction mixture pure water was employed instead using the same procedure.

About 2 grams of the dried solid is accurately weighed and placed in a jar containing 200 cubic centimeters of saline water (.3 N NaCl) and placed on a roller mill for constant agitation for about 16 to 20 hours after which time the swollen gel is weighed blotting excess water from the gel with tissue. The absorption capacity is calculated as follows:

$$\frac{\text{Weight of Swollen Gel}}{\text{Original Sample Weight}} = \text{fluid absorption capacity}$$

In a similar manner, the absorption capacities of a number of other systems were obtained and the values presented in Table I and II below:

TABLE I

PROPERTIES OF COCROSSLINKED POLY(ETHYLENE OXIDE) AND OTHER WATER SOLUBLE POLYMERS

| | | RATIO BY WEIGHT OF POLY(ETHYLENE OXIDE) TO OTHER POLYMERS | | | | | | | | |
| | | 9:1 | | 3:1 | | 1:1 | | 1:3 | | 1:9 | |
| Water Soluble Polymer | Dose in Megarads | % Gel | Cap | % Gel | Cap | % Gel | Cap | % Gel | Cap | % Gel | Cap |
|---|---|---|---|---|---|---|---|---|---|---|---|
| Experimental Starch | .8 | 85 | 30 | 83 | 27 | 72 | 23 | 47 | 21 | 25 | 5 |
| | .6 | 79 | 38 | 82 | 27 | 73 | 29 | 48 | 22 | 12 | 14 |
| | .4 | 78 | 43 | 77 | 39 | 58 | 27 | 49 | 23 | 13 | 12 |
| | .2 | 55 | 72 | 56 | 60 | 51 | 46 | 39 | 28 | 15 | 14 |
| Starch | .8 | 86 | 32 | 86 | 27 | 78 | 23 | 67 | 37 | 33 | 128 |
| | .6 | 86 | 34 | 82 | 33 | 74 | 24 | 64 | 53 | 31 | 80 |
| | .4 | 79 | 45 | 76 | 41 | 70 | 38 | 60 | 70 | 10 | 30 |

TABLE I-continued

PROPERTIES OF COCROSSLINKED POLY(ETHYLENE OXIDE) AND OTHER WATER SOLUBLE POLYMERS

| Water Soluble Polymer | Dose in Megarads | RATIO BY WEIGHT OF POLY(ETHYLENE OXIDE) TO OTHER POLYMERS | | | | | | | | | |
|---|---|---|---|---|---|---|---|---|---|---|---|
| | | 9:1 | | 3:1 | | 1:1 | | 1:3 | | 1:9 | |
| | | % Gel | Cap | % Gel | Cap | % Gel | Cap | % Gel | Cap | % Gel | Cap |
| Hydroxyethylcellulose | .2 | 60 | 94 | 53 | 69 | 53 | 66 | | | | |
| (QP 30,000) | .8 | 89 | 29 | | | 83 | 20 | 83 | 22 | 82 | 19 |
| | .6 | 86 | 39 | | | 80 | 24 | | | 77 | 24 |
| | .4 | 80 | 52 | | | 78 | 35 | 75 | 34 | 69 | 30 |
| | .2 | 66 | 100 | | | 64 | 66 | 55 | 78 | 48 | 69 |
| Hydroxyethylcellulose | .8 | 90 | 29 | 88 | 27 | 89 | 21 | 83 | 21 | 86 | 16 |
| (QP 100-M) | .6 | 84 | 42 | 85 | 36 | 86 | 28 | | | 80 | 23 |
| | .4 | 81 | 54 | 81 | 45 | 83 | 40 | | | 78 | 28 |
| | .2 | 68 | 92 | 41 | 28 | 67 | 67 | 66 | 69 | 62 | 57 |
| Carboxymethylcellulose | .8 | 86 | 32 | 82 | 32 | 80 | 32 | 66 | 29 | 46 | 54 |
| | .6 | 87 | 37 | 80 | 40 | 64 | 37 | 65 | 38 | 45 | 69 |
| | .4 | 76 | 52 | 72 | 48 | 63 | 49 | 58 | 57 | 18 | 93 |
| | .2 | 59 | 85 | 56 | 77 | 46 | 83 | 41 | 89 | | |
| Ethylene-maleic Anhydride | 1.0 | 95 | 22 | 90 | 19 | 89 | 11 | 99 | 25 | 81 | 37 |
| copolymer | .8 | 90 | 25 | 88 | 20 | 84 | 11 | 95 | 37 | 61 | 50 |
| | .6 | 92 | 38 | 91 | 29 | 70 | 15 | 64 | 41 | 53 | 43 |
| | .4 | 92 | 62 | 78 | 59 | 25 | 35 | 53 | 49 | | |
| | .2 | | | | | | | | | | |
| Ammonium Polyacrylate | .8 | 85 | 24 | 86 | 22 | 90 | 22 | 88 | 29 | 77 | 46 |
| | .6 | 80 | 29 | 76 | 28 | 83 | 29 | 82 | 30 | 69 | 57 |
| | .4 | 74 | 32 | 74 | 34 | 85 | 33 | 76 | 47 | 68 | 58 |
| | .2 | 48 | 50 | 55 | 62 | 51 | 64 | 35 | 76 | 44 | 84 |
| Polyacrylamide | .8 | | | 86 | 28 | | | | | | |
| | .6 | | | 81 | 44 | | | | | | |
| | .4 | | | 74 | 50 | | | | | | |
| | .2 | | | 44 | 82 | | | | | | |

TABLE II

PROPERTIES OF COCROSSLINKED POLY(ETHYLENE OXIDE) AND OTHER WATER SOLUBLE POLYMERS

| Water Soluble Polymer | Dose in Megarads | RATIO BY WEIGHT OF POLY(ETHYLENE OXIDE) TO OTHER POLYMERS | | | | | | | |
|---|---|---|---|---|---|---|---|---|---|
| | | 9:1 | | 6:1 | | 4:1 | | 2:1 | |
| | | % Gel | Cap | % Gel | Cap | % Gel | Cap | % Gel | Cap |
| Ethylene-maleic anhydride | .2 | 22 | 90 | 63 | 80 | | | | |
| copolymer - (5 per cent | .4 | 60 | 66 | 58 | 71 | 42 | 64 | 63 | 91 |
| aqueous solution - pH 4.5) | .6 | | | 69 | 46 | 72 | 51 | 65 | 69 |
| | .8 | 80 | 27 | 75 | 40 | 77 | 42 | 76 | 49 |
| Ethylene-maleic anhydride | .2 | | | 45 | 122 | 16 | 264 | | |
| copolymer (10 per cent | .4 | 41 | 76 | 53 | 70 | 51 | 80 | 58 | 136 |
| aqueous solution -pH 4.5) | .6 | 67 | 54 | 68 | 48 | 71 | 64 | 66 | 82 |
| | .8 | 71 | 42 | 80 | 41 | 77 | 50 | 74 | 61 |
| Polyvinyl methylether (10 | .2 | | | | | | | | |
| per cent aqueous solution) | .4 | 48 | 67 | 28 | 70 | 47 | 81 | 40 | 59 |
| | .6 | 57 | 49 | 53 | 67 | 58 | 51 | 62 | 45 |
| | .8 | 62 | 42 | 87 | 58 | 64 | 42 | 65 | 44 |

The following Examples are illustrative:

EXAMPLE II

A 4 per cent stock solution of poly(ethylene oxide) was prepared by dissolving an appropriate amount of coagulant grade poly(ethylene oxide), sold under the trademark "POLYOX" by Union Carbide Corporation; in water under agitation and then shearing the resulting solution to a viscosity of about 500,000 cps.

A 2 per cent solution of poly-4-vinyl-n-butyl pyridinium bromide was prepared by dissolving an appropriate amount of the polymer in water under agitation. The polymer was obtained from the reaction of poly-4-vinyl pyridine with excess n-butyl bromide in ethanol according to known literature synthesis. Twenty grams of 4 per cent poly(ethylene oxide) solution was mixed with 11 grams of 2 per cent poly-4-vinyl-n-butyl pyridinium bromide solution. To obtain a mixture that had a monomer mole ratio of 15:1 (polyethylene oxide: poly-4-vinyl-n-butyl pyridinium bromide). Three grams of this mixture having a pH of 4.9 were poured into a plastic petri dish and irradiated with a 1 MeV van de Graff electron accelerator to a total dose of .7 Mrad. The resulting gel was transferred to a beaker from the dish and allowed to equillibrate with excess water for 24 hours. After this time the gel was weighed and its absorption capacity calculated in accordance with the equation:

$$\frac{\text{weight swollen gel}}{\text{calculated solid content in 3 grams solution}} = \text{absorption capacity}$$

In another case the pH of the solution mixture was adjusted by addition of (a) .1 N HCl to pH 3 and (b) .1 N NaOH to pH 7. Three grams of each of the pH adjusted solution mixtures were irradiated with a 1 MeV van de Graff electron accelerator to a total dose of .7 Mrad. The resulting gels were placed in a beaker with excess water and allowed to equillibrate for 24 hours after which time the gels were weighed and the absorption capacity calculated as above. In a similar manner, the absorption capacities of a number of other systems were obtained and the values presented in Table III below. The water soluble polymers which were co-crosslinked with poly(ethylene oxide) are set forth in the first column.

TABLE III

| COMPOSITION | MEGARADS | MONOMER MOLE RATIO | pH | GEL CAPACITY $\frac{gm\ H_2O}{gm\ solid}$ IN WATER AFTER 24 HOURS |
|---|---|---|---|---|
| PEO-Polyethylene-imine (1) | .7 | 15:1 | 8.4 | 91 |
| | | | 3.5 | 88 |
| | .7 | 20:1 | 8.4 | 77 |
| | | | 3.7 | 89 |
| | .7 | 40:1 | 8.2 | 67 |
| | | | 4.6 | 87 |
| PEO-Poly-4-vinyl-n-butylpyridinium bromide | .7 | 15:1 | 3.0 | 130 |
| | | | 4.9 | 960 |
| | | | 7.0 | 630 |
| | .7 | 20:1 | 3.0 | 130 |
| | | | 7.0 | 890 |
| | .7 | 40:1 | 3.0 | 100 |
| | | | 6.3 | 235 |
| | | | 7.0 | 410 |
| | 1.0 | 20:1 | 5.5 | 469 |
| | | | 10.0 | 416 |
| | 1.0 | 40:1 | 6.1 | 166 |
| | | | 10.4 | 158 |
| PEO-Polyvinyl-alcohol-poly-4-vinyl-n-butyl-pyridinium bromide | 1.0 | 20:20:1 | 5.5 | 365 |
| PEO-Polyvinyl-alcohol-poly-ethyleneimine | 1.0 | 20:20:1 | 7.4 | 60 |
| PEO-Polyvinyl-alcohol-poly-ethyleneimine | 2.0 | 20:1 | 7.4 | 44 |
| | | | 3.3 | 57 |
| | 2.0 | 40:1 | 7.1 | 46 |
| | | | 3.0 | 53 |
| PEO-Polyviny-alcohol-poly-4-vinyl-n-butyl-pyridinium bromide | 2.0 | 20:1 | 5.4 | 592 |
| | | | 10.6 | 324 |
| | 2.0 | 40:1 | 5.4 | 330 |
| | | | 9.9 | 258 |

PEO represents
(1) Poly(ethylene oxide)

EXAMPLE III

A stock solution of poly(ethylene oxide) was prepared by using a commercial grade resin sold by Union Carbide Corporation under the trademark "POLYOX" coagulant resin and having a molecular weight in excess of $10^6$. This resin was dissolved by stirring in water to give a concentration of about 10 per cent then shearing the resultant high viscosity solution in a high speed mixing device to a viscosity of about 1,000,000 cps.

A stock solution of ammonium polyacrylate (commercial grade WS 851 from B. F. Goodrich Chem. Company) was prepared by dissolving this resin in water while stirring to a concentration of about 10 per cent. Mixtures of both resin solutions were prepared at weight ratios (poly(ethylene oxide) : ammonium polyacrylate) of 4:1 and 8:1 were prepared by addition of appropriate volumes of each solution while stirring until a homogeneous blend was obtained.

Each weight ratio mixture was spread out on a polyethylene film backing and the thickness of the solution mixture adjusted with a doctor blade to a wet thickness of approximately 10–12 mils which gave a dry film of about 1 mil thickness. The solution mixture was passed under a van de Graff electron accelerator having an energy of 1.5 MeV and irradiated total doses of 0.4, 0.5 and 0.6 Mrad. Each irradiated mixture was allowed to dry at ambient room temperature and humidity conditions overnight. The resultant films were each analyzed for per cent insolubilized gel content and saline water absorption capacity as outlined in Example II.

In a similar manner irradiated films were prepared of poly(ethylene oxide) mixtures with poly(acrylic acid) adjusted to pH 4.5 and poly-4-vinyl-n-butyl pyridinium bromide. The results are tablulated in Table IV below:

TABLE IV

PROPERTIES OF COCROSSLINKED POLY(ETHYLENE OXIDE) AND OTHER WATER SOLUBLE POLYMERS

| | | RATIO BY WEIGHT OF POLY(ETHYLENE OXIDE) TO OTHER POLYMERS | | | |
|---|---|---|---|---|---|
| | | 4:1 | | 8:1 | |
| WATER SOLUBLE POLYMERS | DOSE IN MEGARADS | % GEL | CAP | % GEL | CAP |
| Ammonium polyacrylate (pH about 7) | .4 | 73.4 | 59 | 66.4 | 59 |
| | .5 | 77.2 | 47 | 72.6 | 49 |
| | .6 | 78.3 | 42 | 78.3 | 41 |
| Poly(vinyl acrylic acid) (pH about 4.5) | .4 | 82.1 | 37 | 80.6 | 47 |
| | .5 | 84.0 | 35 | 81.4 | 38 |
| | .6 | 82.5 | 31 | 83.3 | 36 |

TABLE IV-continued
PROPERTIES OF COCROSSLINKED POLY(ETHYLENE OXIDE) AND OTHER WATER SOLUBLE POLYMERS

| WATER SOLUBLE POLYMERS | DOSE IN MEGARADS | RATIO BY WEIGHT OF POLY(ETHYLENE OXIDE) TO OTHER POLYMERS | | | |
|---|---|---|---|---|---|
| | | 4:1 | | 8:1 | |
| | | % GEL | CAP | % GEL | CAP |
| Poly-4-vinyl-n-butyl pyridinium bromide | .4 | 65.3 | 54 | 68.2 | 45 |
| | .5 | 68.0 | 40 | 69.6 | 41 |
| | .6 | 70.4 | 39 | 70.0 | 35 |

Although the invention has been illustrated by the preceding examples, it is not to be construed as being limited to the materials employed therein, but rather, the invention encompasses the generic area as hereinbefore disclosed. Various modifications and embodiments of this invention can be made without departing from the spirit and scope thereof.

What is claimed is:

1. A process for cocrosslinking at least two water soluble polymers one of which is poly(ethylene oxide) and the other is a second polymer selected from the group consisting of polyacrylic acid, ammonium polyacrylate, vinylmethyl ether-maleic anhydride copolymer and ethylene-maleic anhydride copolymer said process comprising the steps of:
   a. forming an aqueous solution comprising up to 50 per cent by weight of poly(ethylene oxide) and said second polymer,
   b. adjusting the pH of said solution to within the range of from about 2 to about 11,
   c. intimately mixing said solution to form a homogeneous or heterogeneous micro-phase system, and
   d. before any substantial phase separation, exposing said solution to ionizing radiation of a sufficient dosage and for a period of time to form a gel.

2. The cocrosslinked product of claim 1.

3. An absorbent product prepared by drying the cocrosslinked product of claim 2 to remove at least some of the water.

4. A disposable absorbent article containing at least one of said gels prepared by the process of claim 1.

5. The disposable absorbent article of claim 4 which is a catamenial device.

6. The disposable absorbent article of claim 4 which is a sanitary napkin.

7. The disposable absorbent article of claim 4 which is a tampon.

8. The disposable absorbent article of claim 4 which is a diaper.

* * * * *